United States Patent
Birikh et al.

(10) Patent No.: US 11,268,083 B2
(45) Date of Patent: Mar. 8, 2022

(54) GLUCOSE ISOMERASES

(71) Applicant: METGEN OY, Kaarina (FI)

(72) Inventors: Klara Birikh, Kaarina (FI); Anu Minna Maaret Suonpää, Kaarina (FI)

(73) Assignee: METGEN OY, Kaarina (FI)

( * ) Notice: Subject to any disclaimer, the term of this patent is extended or adjusted under 35 U.S.C. 154(b) by 70 days.

(21) Appl. No.: 16/644,231

(22) PCT Filed: Sep. 4, 2018

(86) PCT No.: PCT/EP2018/073747
§ 371 (c)(1),
(2) Date: Mar. 4, 2020

(87) PCT Pub. No.: WO2019/043252
PCT Pub. Date: Mar. 7, 2019

(65) Prior Publication Data
US 2021/0180039 A1    Jun. 17, 2021

(30) Foreign Application Priority Data
Sep. 4, 2017   (EP) ..................... 17189270

(51) Int. Cl.
*C12N 9/92*    (2006.01)
*C12N 1/21*    (2006.01)
*C12P 19/02*   (2006.01)
*C12P 19/24*   (2006.01)

(52) U.S. Cl.
CPC ............. *C12N 9/92* (2013.01); *C12P 19/24* (2013.01); *C12Y 503/01018* (2013.01)

(58) Field of Classification Search
None
See application file for complete search history.

(56) References Cited

FOREIGN PATENT DOCUMENTS

| WO | 2010070549 A1 | 6/2010 |
|----|---------------|--------|
| WO | 2012033926 A1 | 3/2012 |
| WO | 2017060195 A1 | 4/2017 |

OTHER PUBLICATIONS

UniProt Database Accession No. A0A2J6XUM3, Mar. 2018, 1 page (Year: 2018).*
PCT International Search Report and Written Opinion; Application No. PCT/EP2018/073747, Applicant Metgen OY, International filing date of Sep. 4, 2018, dated Oct. 16, 2018, 13 pages.
UniProtKB-B5YAD2, DICTH_1588, Xylose Isomerase, Putative—Dictyoglomus Thermophilum (Strain ATCC 35947 /DSM 3960 / H-6-12)—DICTH 1588 Gene Protein, http://www.uniprot.org/uniprot/B5YAD2, 3 pgs, 2017.
Birikh, Klara R. R, et al. "Chapter 11: MetGen: Value from Wood—Enzymatic Solutions." RSC Catalysis Series, vol. 2018, Royal Society of Chemistry, 2018, pp. 298-321.
Birikh, Klara and Suonpaa, Anu. "New glucose isomerase—fit for biorefinery challenge" Abstract in "Enzyme Engineering XXIV", Pierre Monsan, Toulouse White Biotechnology, France Magali Remaud-Simeon, LISBP-INSA, University of Toulouse, France Eds, ECI Symposium Series, (2017). https://dc.engconfintl.org/enzyme_xxiv/142, 1 page.
UniProtKB-B5YAD2, DICTH_1588, Xylose Isomerase, Putative—Dictyoglomus Thermophilum (Strain ATCC 35947 / DSM 3960 / H-6-12)—DICTH 1588 Gene & Protein, Nov. 25, 2008, XP055413343, http://www.uniprot.org/uniprot/B5YAD2, PCT Authorized Officer Dora Reis Passinhas retrieved from the internet on Oct. 6, 2017, 3 pgs.

* cited by examiner

*Primary Examiner* — David Steadman
(74) *Attorney, Agent, or Firm* — Patent Law Works, LLP

(57) ABSTRACT

The invention is in the field of enzymology. More in particular, it provides a method for the isomerization of glucose into fructose wherein the glucose is derived from lignocellulosic material. More in particular, the invention provides polypeptides encoding mutant glucose isomerase enzymes with improved glucose isomerase activity as compared to the corresponding wild type enzyme. The disclosed polypeptides are particularly suited for converting glucose to fructose in the presence of xylose.

15 Claims, 1 Drawing Sheet
Specification includes a Sequence Listing.

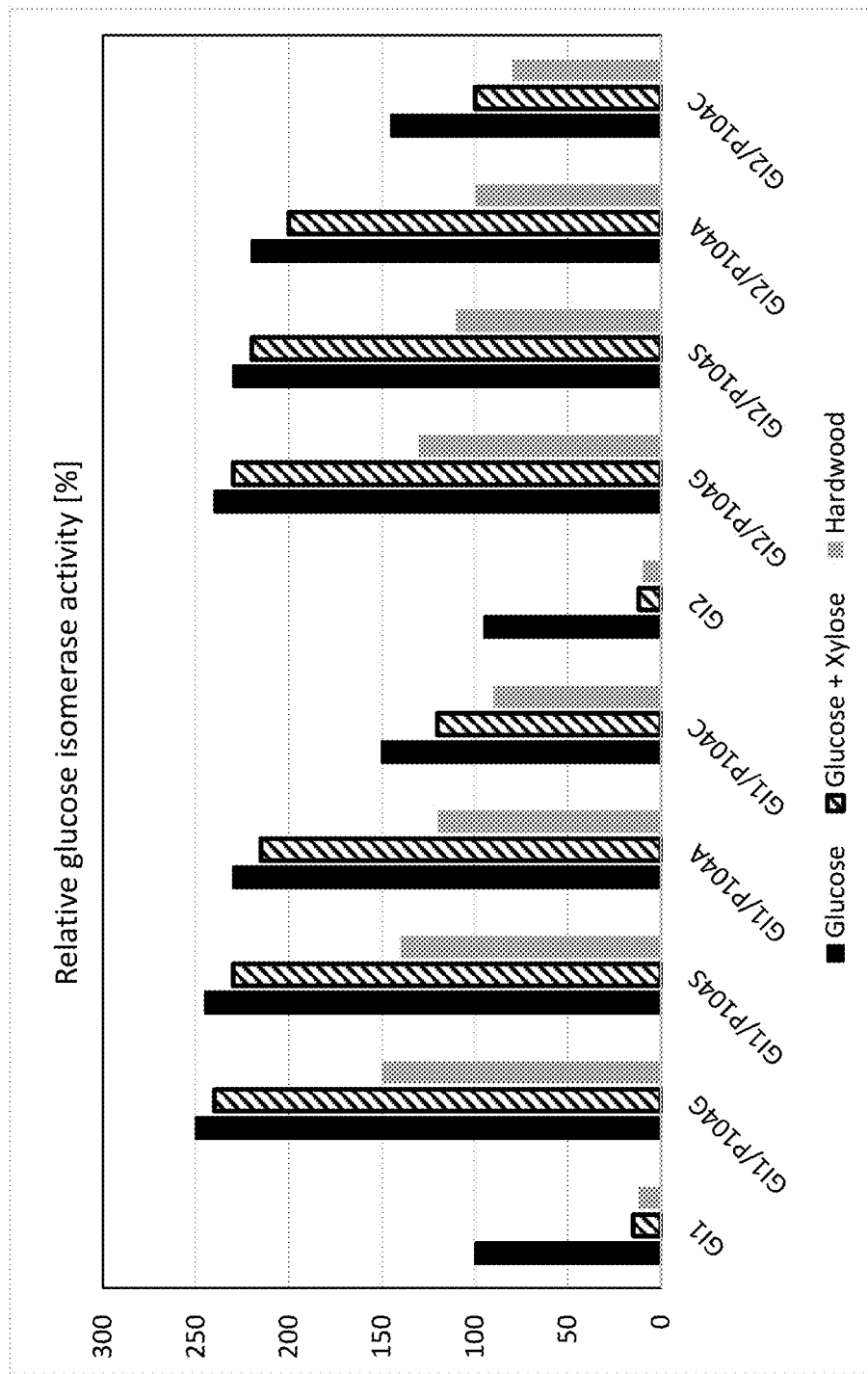

GLUCOSE ISOMERASES

FIELD OF THE INVENTION

The invention is in the field of enzymology. More in particular, it provides a method for the isomerization of glucose into fructose wherein the glucose is derived from lignocellulosic material. It also provides an enzyme with an increased glucose isomerase activity in the presence of xylose. More in particular, the invention provides polypeptides encoding mutant glucose isomerase enzymes with improved glucose isomerase activity as compared to the corresponding wild type enzyme. The disclosed polypeptides are particularly suited for converting glucose to fructose in the presence of xylose.

BACKGROUND OF THE INVENTION

High-fructose corn syrup (HFCS) (also called glucose-fructose, isoglucose and glucose-fructose syrup) is a sweetener made from corn starch that has been processed by an enzyme called glucose isomerase (EC 5.3.1.5) to convert some of its glucose into fructose. HFCS was first marketed in the early 1970s by the Clinton Corn Processing Company, together with the Japanese research institute where the enzyme was discovered.

As a sweetener, HFCS is often compared to granulated sugar. Advantages of HFCS over granulated sugar include being easier to handle, and being less expensive in some countries. In the U.S., HFCS is among the sweeteners that mostly replaced sucrose (table sugar) in the food industry.

In a contemporary process, corn (maize) is milled to produce corn starch and an "acid-enzyme" process is used in which the corn starch solution is acidified to begin breaking up the existing carbohydrates, and then enzymes are added to further metabolize the starch and convert the resulting sugars to fructose.

Glucose isomerase is an enzyme which converts glucose to fructose in a reversible reaction with equilibrium around 1:1 ratio of glucose to fructose. The enzyme may be obtained from many different species of bacteria such as *Streptomyces, Actinoplanes, Microbacterium* and *Bacillus*, and the enzyme is or has been marketed by companies such as Enzyme Bio-systems, Genencor, Gist-Brocades, Solvay Enzyme Inc and Novo Nordisk.

Most successful commercial glucose isomerases are immobilized on a solid support and as a consequence are very stable with an extremely long half life. In a typical process, the immobilized isomerase is loaded in a column and substrate (feed stock) is passed through at a rate that produces an effluent containing 42% fructose. Prerequisite however, is that the feed stock is a refined hydrolysate containing 93-96% glucose. Efficient refining is required in order to remove impurities that could cause inactivation of the glucose isomerase.

Glucose may also be obtained from lignocellulose material. The term "lignocellulose" refers to plant dry matter, so called lignocellulosic biomass. It is the most abundantly available carbon source on earth for the production of bio-fuels, mainly bio-ethanol and potentially bio-based materials such as polymer and plastics. It is composed of carbohydrate polymers (cellulose, hemicellulose), and an aromatic polymer (lignin). These carbohydrate polymers contain different sugar monomers (six- and five-carbon sugars) and they are tightly bound to lignin.

Use of the currently available glucose isomerases in the conversion of lignocellulose-derived glucose into fructose is hampered by the impurities that are present in lignocellulose-derived glucose. These impurities lead to a significant decrease in the stability of the enzyme and cause significant costs for feed stock purification.

Therefore, in order to avoid cumbersome and costly purification steps in the production of fructose from lignocellulose material, it is desirable to have a glucose isomerase that is resistant towards some or most, if not all impurities of lignocellulose-derived glucose, more specifically lignin and xylose.

In a co-pending application (European Patent Application EP 16175234.0) we identified a family of glucose isomerases derived from the genus of Diktyoglomus that were proven to be resistant against the decrease in stability caused by the presence of lignin.

Xylose is a largely preferred substrate for glucose isomerase, as compared to glucose. Thus, xylose competes with glucose for the enzyme and glucose conversion rate is thereby largely reduced. It is therefore desirable to have an enzyme with a glucose isomerase activity that is less or not at all inhibited by xylose.

SUMMARY OF THE INVENTION

The current invention discloses glucose isomerases that are resistant to inhibition by the presence of xylose in the reaction mixture and variants thereof. Thus the invention provides polypeptides encoding glucose isomerase enzymes with an increased or improved glucose isomerase activity.

The term "improved glucose isomerase activity" or "increased glucose isomerase activity" as used herein refers to an enzyme with a higher glucose isomerase activity as compared to a control enzyme. In other words, this means that the same amount of enzyme (expressed as mass of protein) is able to convert more glucose to fructose per minute as compared to a control enzyme.

More in particular, the invention provides a polypeptide with glucose isomerase activity comprising an amino acid sequence that is at least 90% identical to the amino acid sequence according to SEQ ID NO: 1 or SEQ ID NO: 2, wherein the polypeptide comprises a tiny amino acid residue at an amino acid position corresponding to position 104 in SEQ ID NO: 1 or SEQ ID NO: 2.

This enzyme exhibits an improved glucose isomerase activity as compared to the control enzyme; i.e. wherein the control enzyme is the glucose isomerase according to SEQ ID NO: 1 or SEQ ID NO: 2 wherein the amino acid corresponding to position 104 is not a tiny amino acid.

In a preferred embodiment, the term "tiny amino acid" as used herein refers to amino acids selected from the group consisting of glycine, alanine, serine and cysteine.

The invention also relates to a composition comprising a polypeptide as described above, a nucleic acid encoding a polypeptide as described above, a vector comprising such a nucleic acid and a composition comprising such a nucleic acid or a vector.

The invention also provides a recombinant host cell comprising a nucleic acid, a vector or a composition as described above.

Moreover, the invention relates to a method for producing a polypeptide as described above, comprising the steps of: culturing a recombinant host cell as described above, under conditions suitable for the production of the polypeptide, and recovering the polypeptide obtained, and optionally purifying the polypeptide.

In addition, the invention relates to a method of using a polypeptide as described above for converting glucose to fructose.

The invention also relates to a method for improving the glucose to fructose conversion in the presence of xylose by a polypeptide comprising an amino acid sequence that is at least 90% identical to the amino acid according to SEQ ID NO: 1 or SEQ ID NO: 2, the method comprising the step of altering the amino acid at a position corresponding to position 104 in SEQ ID NO: 1 or SEQ ID NO: 2 to a tiny amino acid residue.

Exemplified herein are improved glucose isomerases comprising an amino acid sequence according to SEQ ID NO: 1, wherein single amino acid substitutions have been made in order to arrive at glucose isomerases P104G, P104S, P104A and P104C. This annotation is used herein to indicate a replacement of the amino acid residue Proline (P), corresponding to position 104 of SEQ ID NO: 1, with either one of the residues G (glycine), S (serine), A (alanine) or C (cysteine), thereby obtaining the polypeptides according to SEQ ID NO: 3, SEQ ID NO: 4, SEQ ID NO: 5 and SEQ ID NO: 6, respectively.

Also exemplified are similar substitutions in a glucose isomerase comprising the amino acid sequence according to SEQ ID NO: 2, wherein glucose isomerases P104G, P104S, P104A and P104C are obtained, the amino acid sequences of which are represented by SEQ ID NO: 7, SEQ ID NO: 8, SEQ ID NO: 9 and SEQ ID NO: 10 respectively.

DNA sequences encoding amino acid sequences SEQ ID NO: 1 through SEQ ID NO: 10 are represented by SEQ ID NO: 11 through SEQ ID NO: 20.

LEGEND TO THE FIGURE

FIG. 1: Diagram showing the relative glucose isomerase activity of polypeptides comprising the amino acid sequence according to SEQ ID NO: 1 (WT, annotated as GI1), SEQ ID NO: 2 (WT, annotated as GI2) and SEQ ID NO: 3 (GI1/P104G), SEQ ID NO: 4 (GI1/P104S), SEQ ID NO: 5 (GI1/P104A), SEQ ID NO: 6 (GI1/P104C), SEQ ID NO: 7 (GI2/P104G), SEQ ID NO: 8 (GI2/P104S), SEQ ID NO: 9 (GI2/P104A), SEQ ID NO: 10 (GI2/P104C) on various substrates, see example 4.

Glucose isomerase activity was determined using a substrate containing 200 mM glucose (labelled "Glucose") and compared to a substrate containing 200 mM Glucose and 20 mM xylose (labelled "Glucose+Xylose", see Example 4) as well as a hardwood hydrolysate comprising 42 mM xylose (see example 6).

DETAILED DESCRIPTION OF THE INVENTION

In enzymology, a glucose isomerase (EC 5.3.1.5) is an enzyme that catalyzes the interconversion of D-glucose and D-fructose. This enzyme belongs to the family of isomerases, specifically those intramolecular oxidoreductases interconverting aldoses and ketoses. The glucose isomerase has now been observed in nearly a hundred species of bacteria. The systematic name of this enzyme class is D-xylose aldose-ketose-isomerase. Other names in common use include D-xylose isomerase, D-xylose ketoisomerase, and D-xylose ketol-isomerase. In industry, these enzymes are mostly referred to as glucose-isomerases due to their industrial use to produce fructose from glucose. However, xylose is a preferred substrate for these enzymes and the presence of xylose is highly inhibiting glucose isomerization.

The commercially available glucose isomerase enzymes have been used successfully in the production of high fructose corn syrup (HFCS) from starch, but they are not suited for the isomerisation of glucose obtained from lignocellulose material. Such lignocellulose derived glucose is characterized by the presence of lignin and other sugars derived from hemicelluloses including xylose.

Lignocellulosic biomass is the most abundantly available carbon source on earth for the production of biofuels, mainly bio-ethanol and potentially also for the production of bio-based materials such as polymers and plastics. It is composed of carbohydrate polymers (cellulose, hemicellulose), and an aromatic polymer (lignin). Cellulose consists of linear glucose polymers, whereas hemicellulose is a branched heterogeneous polymer consisting of various 6- and 5-carbon sugars depending on the biological species.

Hemicellulose derived from softwood contains mostly glucomannans, while hemicellulose derived from hardwood contains mostly glucuronoxylans. Thus hydrolysate of hardwood usually contains a considerable amount of xylose (Sjostrom, E., Wood Chemistry. Fundamentals and Applications. Second edition ed. 1993, San Diego: Academic press. 292.).

In our co-pending European Patent Application EP 16175234.0 it was shown that wild type glucose isomerases GI1 and GI2 are efficiently functioning in softwood hydrolysate, where they are resistant to lignin and other impurities. However, hardwood presents an additional hurdle, namely xylose. Xylose is a much-preferred substrate for these type of enzymes, and reaction being reversible the xylose is not spent during the course of the reaction and poses continuous inhibition.

We herein indeed confirmed that the glucose isomerases derived from *Dictyoglomus thermophilum* and *Dictyoglomus turgidum* according to SEQ ID NO: 1 and SEQ ID NO: 2 were suitable for the conversion of glucose to fructose in a solution containing glucose, however, they were strongly inhibited by the presence of xylose such as present in hardwood hydrolysates (FIG. 1).

We found that GI1 and GI2 activities were reduced in the presence of xylose (i.e. in a solution of glucose plus xylose), reductions to 10-15% of their activity in pure glucose were observed. In line with these findings, the activity of both glucose isomerases was reduced to less than 12% when a hydrolysate of hardwood was used as the substrate (Table 1, FIG. 1).

Hardwood comes from angiosperm—or flowering plants—such as birch, *eucalyptus*, oak, maple, or walnut, which are not monocots. Other examples of hardwood include but are not limited to alder, balsa, beech, hickory, mahogany, and teak.

Surprisingly, we found that a single mutation in the wild type glucose isomerases GI1 and GI2 at position 104 substituting the wild type amino acid Proline with a tiny amino acid such as glycine, alanine, serine, or cysteine, makes glucose isomerization much less inhibited by xylose. Moreover, it tremendously improved the activity of the glucose isomerase to a value between 150 and 250% (Table 1).

TABLE 1

Relative glucose isomerase activity of GI1 and GI2 in different substrates

| | Glucose [% activity] | Glucose + Xylose [% activity] | Hardwood [% activity] |
|---|---|---|---|
| GI1 | 100 | 15 | 12 |
| GI1/P104G | 250 | 240 | 150 |
| GI1/P104S | 245 | 230 | 140 |
| GI1/P104A | 230 | 215 | 120 |
| GI1/P104C | 150 | 120 | 90 |
| GI2 | 95 | 12 | 10 |
| GI2/P104G | 240 | 230 | 130 |
| GI2/P104S | 230 | 220 | 110 |
| GI2/P104A | 220 | 200 | 100 |
| GI2/P104C | 145 | 100 | 80 |

In conclusion, wild type glucose isomerase activity of enzymes GI1 and GI2 in 200 mM glucose was greatly reduced in the presence of 20 mM xylose. In contrast, glucose isomerase enzymes carrying one of the above mentioned mutations at position 104 were more active than the wild type enzymes in the presence of xylose (table 1, FIG. 1, example 4). Moreover, enzymes with mutations at position 104 showed 1.5 to 2.5 fold higher glucose isomerization activity as compared to wild type enzymes at the same enzyme dosage (FIG. 1).

Next, we tested the mutated enzymes in the isomerization of glucose in crude lignocellulosic hydrolysates of hardwood (example 6). Hardwood hydrolysate, containing higher levels of xylose than softwood, greatly inhibited the glucose isomerase activity of the wild type enzymes GI1 and GI2, but not that of the mutated enzymes. Mutated enzymes demonstrated a clear glucose isomerase activity in hardwood hydrolysates, making them exceptionally suited for the conversion of glucose into fructose in lignocellulose-derived material, in particular when the lignocellulose is derived from wood such as wood with a high xylose content, such as hardwood.

The term "mutated enzyme" as used herein refers to a glucose isomerase enzyme comprising an amino acid sequence according to SEQ ID NO: 1 or SEQ ID NO: 2, wherein the amino acid at a position corresponding to the position 104 of SEQ ID NO: 1, or SEQ ID NO: 2 (proline in SEQ ID NO: 1 or SEQ ID NO: 2) is replaced by a tiny amino acid.

The term "tiny amino acid" as used herein indicates an amino acid with a tiny side group. In other words, these amino acids are smaller than 110 Angstrom or 11 nanometer. imgt.org/IMGTeducation/Aide-memoire/_UK/aminoacids/IMGTclasses.html. Preferred examples of tiny amino acids are amino acids G (glycine), A (alanine), S (serine) and C (cysteine).

Glucose isomerases (GIs) according to SEQ ID NO: 1 and SEQ ID NO: 2 are homologous sequences with an amino acid sequence identity of 98%. It may therefore be expected that closely related GIs, such as GIs with an amino acid sequence that is at least 90% such as 91%, 92%, 93%, 94%, 95%, 96%, 97%, 98% or even 99% identical with either SEQ ID NO: 1 or SEQ ID NO: 2, will perform in the same way as GI1 and GI2 exemplified herein. Such close homologues may be obtained from natural sources or by directed mutagenesis. The skilled person is well aware of materials and methods for obtaining such close homologues.

As used herein, the degree of identity between two or more amino acid sequences is equivalent to a function of the number of identical positions shared by the sequences (i.e., % identity=number of identical positions divided by the total number of aligned positions×100), excluding gaps, which need to be introduced for optimal alignment of the two sequences, and overhangs. The comparison of sequences and determination of percent identity between two or more sequences can be accomplished using standard methods known in the art. For example, a freeware conventionally used for this purpose is "Align" tool at NCBI recourse blast.ncbi.nlm.nih.gov/Blast.cgi?PAGE_TYPE=BlastSearch&BLAST_SPEC=blast2seq&LINK_LOC=align2seq Introduction of a specific mutation in a recombinant gene is also among the routine skills of a molecular biologist. Specific guidance may be obtained from Methods in Molecular Biology Vol 182, "In vitro mutagenesis protocols", Eds Jeff Braman, Humana Press 2002. There are commercially available kits for performing site-directed mutagenesis (for example, QuikChange II XL Site-Directed Mutagenesis kit Agilent Technologies cat No 200521).

Hence, the invention relates to a polypeptide with glucose isomerase activity comprising an amino acid sequence that is at least 90% identical to the amino acid according to SEQ ID NO: 1 or SEQ ID NO: 2, wherein the polypeptide comprises a tiny amino acid residue at an amino acid position corresponding to position 104 in SEQ ID NO: 1 or SEQ ID NO: 2.

The phrase "an amino acid position corresponding to position 104 in SEQ ID NO: 1 or SEQ ID NO: 2" is in itself sufficiently clear for the skilled person. In order to avoid any misunderstanding, the following is provided. The phrase "an amino acid position corresponding to position 104 in SEQ ID NO: 1 or SEQ ID NO: 2" is used herein to indicate a certain position in the amino acid sequence of the polypeptide with glucose isomerase activity. That certain position is to be determined by aligning the sequence of the polypeptide with glucose isomerase activity with the sequence of either SEQ ID NO: 1 or SEQ ID NO: 2 as described above. The amino acid position in the polypeptide with glucose isomerase that aligns with the amino acid at position 104 in SEQ ID NO: 1 or SEQ ID NO: 2 is then referred to as the amino acid position corresponding to position 104 in SEQ ID NO: 1 or SEQ ID NO: 2.

The invention also relates to a method for the interconversion of D-glucose and D-fructose in the presence of a glucose isomerase, wherein the D-glucose is derived from lignocellulose-containing biomass, and wherein the glucose isomerase is a glucose isomerase according to the invention.

The phrase "glucose derived from lignocellulose-containing material" is equivalent to the term "lignocellulose-derived glucose". Both are used herein to indicate that the glucose is contained in a solution comprising other sugars, in particular xylose, derived from the lignocellulosic material, such as lignocellulosic biomass. As such, the term is used to distinguish the glucose from purified glucose, which does not contain xylose.

Mutated variants of GI1 and GI2 as disclosed herein and their homologues with at least 90% sequence identity provide advantageous results in comparison to other GIs in conditions wherein the substrate solution comprises xylose. Not only are the mutant enzymes resistant against the presence of xylose in a composition comprising glucose and xylose, they are also more active, even up to 2.5 times more active in converting glucose into fructose.

In other terms, the invention relates to a process for converting glucose into fructose comprising the steps of:
  a) providing a solution or suspension comprising glucose and xylose b) enzymatically converting the glucose to fructose in the presence of a glucose isomerase, c) optionally purifying the fructose from the solution, wherein the glucose isomerase comprises an amino acid sequence that is at least 90% identical with the sequence according to SEQ ID NO: 1 or SEQ ID NO: 2 and wherein the glucose isomerase comprises a tiny amino acid residue at an amino acid position corresponding to position 104 in SEQ ID NO: 1 or SEQ ID NO: 2.

The solution or suspension comprising glucose and xylose may advantageously be obtained by hydrolyzing a hardwood biomass. Such hydrolysis is advantageously performed enzymatically, for instance by employing a cellulase.

Advantageously, the pretreatment step comprises a steam explosion step and/or an acid pretreatment step.

All these steps are well known in the art and the skilled person is well aware of the metes and bounds of the terms used herein.

The invention may have particular advantages when the enzyme is used in a solution or suspension that contains xylose in a concentration that inhibits the activity of the wild type enzyme according to SEQ ID NO: 1 or SEQ ID NO: 2 for 10% or more, such as 20%, 30%, 40%, 50% or more, such as 60%, 70%, 80%, 90% or even more like 95% or more.

The polypeptides as described herein may be used in compositions containing several additional components, such as stabilizers, fillers, cell debris, culture medium etcetera. Hence, the invention provides a composition comprising a polypeptide as described herein.

Polypeptides as described herein may be obtained by expressing a recombinant DNA in a heterologous expression system. The term "heterologous expression system" or equivalent means a system for expressing a DNA sequence from one host organism in a recipient organism from a different species or genus than the host organism. The most prevalent recipients, known as heterologous expression systems, are chosen usually because they are easy to transfer DNA into or because they allow for a simpler assessment of the protein's function. Heterologous expression systems are also preferably used because they allow the upscaling of the production of a protein encoded by the DNA sequence in an industrial process. Preferred recipient organisms for use as heterologous expression systems include bacterial, fungal and yeast organisms, such as for example *Escherichia coli*, *Bacillus*, *Corynebacterium*, *Pseudomonas*, *Pichia pastoris*, *Saccharomyces cerevisiae*, *Yarrowia lipolytica*, filamentous fungi and many more systems well known in the art.

The presently disclosed polypeptides or proteins may be fused to additional sequences, by attaching or inserting, including, but not limited to, affinity tags, facilitating protein purification (S-tag, maltose binding domain, chitin binding domain), domains or sequences assisting folding (such as thioredoxin domain, SUMO protein), sequences affecting protein localization (periplasmic localization signals etc), proteins bearing additional function, such as green fluorescent protein (GFP), or sequences representing another enzymatic activity. Other suitable fusion partners for the presently disclosed polypeptides are known to those skilled in the art.

The present invention also relates to polynucleotides encoding any of the glucose isomerase variants disclosed herein. Means and methods for cloning and isolating such polynucleotides are well known in the art.

Furthermore, the present invention relates to a vector comprising a polynucleotide according to the invention, optionally operably linked to one or more control sequences. Suitable control sequences are readily available in the art and include, but are not limited to, promoter, leader, polyadenylation, and signal sequences.

Glucose isomerase variants according to various embodiments of the present invention may be obtained by standard recombinant methods known in the art. Briefly, such a method may comprise the steps of: culturing a recombinant host cell as described above under conditions suitable for the production of the polypeptide, and recovering the polypeptide obtained. The polypeptide may then optionally be further purified.

A large number of vector-host systems known in the art may be used for recombinant production of the glucose isomerases as described herein. Possible vectors include, but are not limited to, plasmids or modified viruses which are maintained in the host cell as autonomous DNA molecule or integrated in genomic DNA. The vector system must be compatible with the host cell used as is well known in the art. Non-limiting examples of suitable host cells include bacteria (e.g. *E. coli*, bacilli), yeast (e.g. *Pichia Pastoris*, *Saccharomyces Cerevisiae*), fungi (e.g. filamentous fungi) insect cells (e.g. Sf9).

In yet other terms, the invention relates to a method for improving glucose isomerization, especially in the presence of xylose, of a polypeptide with glucose isomerase activity comprising an amino acid sequence that is at least 90% identical to the amino acid according to SEQ ID NO: 1 or SEQ ID NO: 2, the method comprising the step of altering the amino acid at a position corresponding to position 104 in SEQ ID NO: 1 or SEQ ID NO: 2 to a tiny amino acid residue.

EXAMPLES

Example 1: Preparation of Polypeptides According to SEQ ID NO: 1-10 and Nucleotides According to SEQ ID NO: 11-20

The DNA constructs according to SEQ ID NO: 11 and SEQ ID NO: 12 encoding the polypeptides according to SEQ ID NO: 1, SEQ ID NO: 2 were designed using codon frequencies optimized for expression in *E. coli* and commercially synthesized and cloned into a plasmid vector based on a standard pET28a+ plasmid. The plasmid vector contained an N-terminal nucleotide sequence encoding peptidyl-prolyl isomerase from Enterobacteriaceae (Protein databank accession number WP_000255997.1). The recombinant gene was expressed in *Escherichia coli* BL21(DE3) under the control of the T7-RNA-polymerase promoter (see Example 2). This resulted in expression of the recombinant proteins with an N-terminal tag. Nucleotide sequences according to SEQ ID NO: 13-20 encoding the glucose isomerases according to SEQ ID NO: 3-10 were ordered commercially and expressed in the same way as described herein.

Example 2: Heterologous Expression of Polypeptides with Glucose Isomerase Activity Protein production was carried out in *E. coli* BL21(DE3) strain according to the plasmid manufacturer protocol available at richsingiser.com/4402/Novagen%20pET%020system%/20manual.pdf. The incubation temperature for protein production was 30 degrees Celsius, which was found optimal for maximum yield of the active protein. Cells were lysed using lysis buffer (50 mM Tris-HCl pH7.4, 1% Triton X100, 1 mM CoCl2) and heated at 70 degrees Celsius for 30 min. The glucose isomerase activity was detected in the insoluble fraction only, and could be fully recovered by centrifugation. Thus, thermostable recombinant glucose isomerase was expressed in active insoluble form allowing reuse of the enzyme in several reaction batches. Mutations at position corresponding to position 104 of GI1 or GI-2 did not detectably effect the expression level of the recombinant proteins, they were essentially the same as the expression levels of the wild type enzymes comprising amino acid sequences according to SEQ ID NO: 1 or SEQ ID NO: 2.

Example 3: Glucose Isomerase Activity Assay

Glucose isomerase activity (isomerization reaction rate) was determined by measuring fructose level in the reaction mixture according to the protocol described in Schenk and Bisswanger, A microplate assay for D-xylose/D-glucose isomerase. Enzyme and Microbial Technology (Elsevier Science Inc, N Y, 1998), V22, pp. 721-723.

Measurement was performed in the linear stage of the reaction course (product accumulation is linear with time). Ten-microliter aliquots of the reaction mixture were taken and pipette into a 96-well plate, 40 ul of water was added resulting in 50 ul sample. In some cases, higher dilution of the reaction mixture with water was used to prepare 50 ul of the diluted sample to match the dynamic range of the method. 150 ml of a freshly prepared 1:1 mixture (v/v) of solution A (0.05% resorcinol in ethanol) and solution B (0.216 g FeNH4(SO4)2*12 H2O in 1 l concentrated HCl) were added. For color development, the plate was incubated at 80° C. for 40 min. The absorbance was measured with a microplate reader (Thermo) at 490 nm.

It has to be noted that the presence of xylose or its isomerization product xylulose does not affect the measurement of fructose by this method.

Example 4 Glucose Isomerization Activity and Xylose Inhibition of Polypeptides Comprising SEQ ID NO: 1-10 in Pure Glucose Solution with and without Xylose In this experiment, we compared wild type glucose isomerases: GI1 (SEQ ID NO: 1) and GI2 (SEQ ID NO: 2) to glucose isomerases mutants P104G, P104S, P104A and P104C of both these sequences.

Enzymatic activity of the wild type enzyme (GI1 and GI2) and mutants thereof was first determined in a glucose solution (200 mM Glucose, 10 mM MOPS pH 8.0, 1 mM MgCl2).

A parallel set of reactions had the same composition apart from additionally comprising 20 mM xylose. The enzyme dosage was selected so that during the reaction time of 1 h (at 70 degrees C.), the product formation remained linear in all reactions. All enzymes were used at the same dosage (in micrograms of recombinant protein per ml of reaction). Glucose isomerization activity was measured as described in Example 3.

The results are shown in table 1 and depicted in FIG. 1. Glucose isomerase activity of the wild type enzyme without xylose in the reaction mixture was taken as 100%, and activities in the presence of xylose as well as mutated enzymes activities in the presence or absence of xylose were calculated as percentage of this value.

Mutated glucose isomerases according to the invention showed much higher glucose isomerization activity (150-250% of the wild type). In addition, it was found that glucose isomerases according to the invention showed little or no sensitivity to the presence of xylose.

Example 5 Preparation of Lignocellulose Hydrolysate

Wood chips, obtained from birch (hardwood), were submerged in 2% sulfuric acid at a dry matter content of 20% and subjected to a steam explosion pretreatment essentially as described in European patent application EP 2623607A1. The pretreated material in its entirety (without removing solubilized fractions of hemicellulose and lignin) was subjected to enzymatic hydrolysis using Cellic® CTec3 cellulase product from Novozymes. The hydrolysis was carried out under the manufacturers recommended conditions (incubation for 72 h at 55 degrees Celsius, pH 5.5 at 10% solids content), remaining solids were removed from the hydrolysis mixture by centrifugation, the liquid fraction was then evaporated to approximately 100 g/L sugar concentration, and the pH was adjusted to 8 with sodium hydroxide. The resulting solution is referred to herein further as "hydrolysate" or "lignocellulose hydrolysate" and used for the isomerization reaction. The resulting hardwood hydrolysate contained the following sugar composition: 68 g/L glucose, 12 g/l xylose and less than 1 g/L other sugars Example 6 Glucose Isomerization Activity and Xylose Inhibition of Polypeptides Comprising SEQ ID NO: 1-10 in Lignocellulose Hydrolysates of Hardwood In this experiment, we compared wild type glucose isomerases: GI1 (SEQ ID NO: 1) and GI2 (SEQ ID NO: 2) with mutant variants P104G, P104S, P104A and P104C of both glucose isomerases for isomerization of glucose to fructose in crude hydrolysate of hardwood.

For this experiment, the lignocellulose hydrolysates (see example 5) were diluted with water to an end concentration of 200 mM glucose (resulting in 42 mM xylose concentration) and brought to 10 mM MOPS pH 8.0 and 1 mM MgCl2. Enzymes were added to the reaction mixtures at the same dosages as in Example 4 and reactions carried out for 1 h at 70 degrees C. The results are shown in FIG. 1. For each enzyme, activity in 200 mM glucose solution without xylose as described above was taken as 100% and activity in hardwood hydrolysate was plotted as a percentage of that.

Both wild type enzymes were strongly inhibited in the hardwood hydrolysate, like they were in the glucose plus xylose solution described above. However, mutant enzymes were showing higher activities in both the glucose plus xylose model solution as in the hardwood hydrolysate (table 1, FIG. 1).

The invention claimed is:

1. A polypeptide with glucose isomerase activity, wherein the polypeptide comprises:
   an amino acid sequence that has at least 90% sequence identity to the full length of the amino acid sequence of SEQ ID NO: 1 or SEQ ID NO: 2,
   wherein the polypeptide comprises a Glycine, Serine, Alanine or Cysteine residue at a position corresponding to position 104 in SEQ ID NO: 1 or SEQ ID NO: 2.

2. The polypeptide of claim 1, wherein the polypeptide comprises a Glycine residue at a position corresponding to position 104 in SEQ ID NO: 1 or SEQ ID NO: 2.

3. The polypeptide of claim 1, wherein the polypeptide comprises an amino acid sequence that has at least 90% sequence identity to the full length of the amino acid sequence of SEQ ID NO: 1.

4. The polypeptide of claim 1, wherein the polypeptide is an isolated polypeptide.

5. A nucleic acid comprising a nucleotide sequence encoding the polypeptide of claim 1.

6. A vector comprising the nucleic acid of claim 5.

7. An isolated recombinant host cell comprising the nucleic acid of claim 5.

8. The recombinant host cell of claim 7, wherein the host cell is selected from the group consisting of *Escherichia coli*, *Bacillus*, *Corynebacterium*, *Pseudomonas*, *Pichia pastoris*, *Saccharomyces cerevisiae*, *Yarrowia lipolytica*, filamentous fungi, yeast, and insect cells.

9. A method for producing the polypeptide of claim 1, the method comprising:
   culturing a recombinant host cell comprising a nucleic acid encoding the polypeptide of claim 1 under conditions suitable for the production of the polypeptide, and
   recovering the polypeptide, and
   optionally purifying the polypeptide.

10. A method of converting glucose derived from lignocellulosic biomass to fructose, the method comprising:
    contacting the polypeptide of claim 1 with the glucose, thereby converting the glucose to fructose.

11. The method of claim 10, wherein the lignocellulosic biomass contains xylan or glucurono-xylan.

12. The method of claim 10, wherein the lignocellulosic biomass is wood.

13. The polypeptide of claim 1, wherein the polypeptide comprises an amino acid sequence that has at least 91%, 92%, 93%, 94%, 95%, 96%, 97%, 98%, or 99% sequence identity to the full length of the amino acid sequence of SEQ ID NO: 1.

14. The polypeptide of claim 1, wherein the polypeptide comprises an amino acid sequence that has at least 91%, 92%, 93%, 94%, 95%, 96%, 97%, 98%, or 99% sequence identity to the full length of the amino acid sequence of SEQ ID NO: 2.

15. The method of claim 12, wherein the wood is hardwood.

* * * * *

SEQUENCE LISTING

<160> NUMBER OF SEQ ID NOS: 20

<210> SEQ ID NO 1

<211> LENGTH: 368
<212> TYPE: PRT
<213> ORGANISM: Dictyoglomus thermophilum

<400> SEQUENCE: 1

Met Pro Phe Val Asp His Arg Ala Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Ser Ile Pro Glu Arg Ile Glu Met Ala Ala Glu
    50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Pro Leu Ser Leu Phe Tyr Asp Lys Ile
            100                 105                 110

Phe Glu Phe Gly Ser Leu Ser Asn Pro Tyr Glu Lys Tyr Arg Lys Val
        115                 120                 125

Ala Tyr Glu Arg Leu Val Asn Gly Leu Lys Leu Val Lys Glu Ala Asn
    130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
    290                 295                 300

Gln Gly Tyr Phe Gly Ile Asp Ile Asn Pro Glu Arg Met Pro Val Ile
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Lys
        355                 360                 365

<210> SEQ ID NO 2
<211> LENGTH: 368
<212> TYPE: PRT

<213> ORGANISM: Dictyoglomus thermophilum

<400> SEQUENCE: 2

Met Pro Phe Val Asp His Arg Asn Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Gly Ile Pro Glu Arg Ile Glu Met Ala Ala Glu
    50                  55                  60

Met Ala Lys Tyr Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Thr
                85                  90                  95

Gly Ile Arg Leu Val Ala Val Pro Leu Ser Leu Phe Tyr Asp Lys Ile
            100                 105                 110

Phe Glu Phe Gly Ser Leu Ser Asn Pro Tyr Glu Lys Tyr Arg Lys Ile
        115                 120                 125

Ala Tyr Glu Arg Leu Val Asn Gly Leu Lys Leu Val Lys Glu Ala Asn
    130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
290                 295                 300

Gln Gly Tyr Phe Gly Ile Asp Ile Asn Pro Glu Arg Ile Pro Val Val
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Arg
        355                 360                 365

<210> SEQ ID NO 3
<211> LENGTH: 368
<212> TYPE: PRT
<213> ORGANISM: Dictyoglomus thermophilum

<400> SEQUENCE: 3

Met Pro Phe Val Asp His Arg Ala Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Ser Ile Pro Glu Arg Ile Glu Met Ala Ala Glu
    50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Gly Leu Ser Leu Phe Tyr Asp Lys Ile
            100                 105                 110

Phe Glu Phe Gly Ser Leu Ser Asn Pro Tyr Glu Lys Tyr Arg Lys Val
        115                 120                 125

Ala Tyr Glu Arg Leu Val Asn Gly Leu Lys Leu Val Lys Glu Ala Asn
    130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
290                 295                 300

Gln Gly Tyr Phe Gly Ile Asp Ile Asn Pro Glu Arg Met Pro Val Ile
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Lys
        355                 360                 365

<210> SEQ ID NO 4
<211> LENGTH: 368
<212> TYPE: PRT
<213> ORGANISM: Dictyoglomus thermophilum

<400> SEQUENCE: 4

Met Pro Phe Val Asp His Arg Ala Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Ser Ile Pro Glu Arg Ile Glu Met Ala Ala Glu
    50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Ser Leu Ser Leu Phe Tyr Asp Lys Ile
            100                 105                 110

Phe Glu Phe Gly Ser Leu Ser Asn Pro Tyr Glu Lys Tyr Arg Lys Val
            115                 120                 125

Ala Tyr Glu Arg Leu Val Asn Gly Leu Lys Leu Val Lys Glu Ala Asn
            130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
            195                 200                 205

Gly Ile Leu Ala Ala Arg Asp Ile Glu Ala Arg Leu Lys Asn Pro Glu
210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
            245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
            275                 280                 285

Trp Asp Ser Thr Glu Ala Leu Leu Tyr Thr Leu Lys Met Val Gly Tyr
    290                 295                 300

Gln Gly Tyr Phe Gly Ile Asp Ile Asn Pro Glu Arg Met Pro Val Ile
305                 310                 315                 320

Lys Ala Ile Glu Ile Asn Thr Lys Val Leu Gln Ile Met Asn Glu Arg
            325                 330                 335

Ile Glu Arg Leu Pro His Asp Arg Ile Ile Glu Cys Tyr Phe Asp Pro
            340                 345                 350

Glu Asn His Arg Gly Glu Leu Gly Leu Ile Leu Ala Glu Asn His Lys
            355                 360                 365

<210> SEQ ID NO 5
<211> LENGTH: 368
<212> TYPE: PRT
<213> ORGANISM: Dictyoglomus thermophilum

<400> SEQUENCE: 5

Met Pro Phe Val Asp His Arg Ala Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
        35                  40                  45

Tyr Val Glu Gln Lys Ser Ile Pro Glu Arg Ile Glu Met Ala Ala Glu
    50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Ala Leu Ser Leu Phe Tyr Asp Lys Ile
            100                 105                 110

Phe Glu Phe Gly Ser Leu Ser Asn Pro Tyr Glu Lys Tyr Arg Lys Val
            115                 120                 125

Ala Tyr Glu Arg Leu Val Asn Gly Leu Lys Leu Val Lys Glu Ala Asn
130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
290                 295                 300

Gln Gly Tyr Phe Gly Ile Asp Ile Asn Pro Glu Arg Met Pro Val Ile
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Lys
        355                 360                 365

<210> SEQ ID NO 6
<211> LENGTH: 368
<212> TYPE: PRT
<213> ORGANISM: Dictyoglomus thermophilum

<400> SEQUENCE: 6

Met Pro Phe Val Asp His Arg Ala Gln Lys Ile Arg Arg Ser Lys Glu
1               5                   10                  15

Glu Leu Leu Lys His Met Gln Thr Phe Lys Leu Asp Leu Lys Phe Ser

```
            20                  25                  30
Val Gly Ile Trp Tyr Phe Thr Pro Gly Gly Arg Phe His Glu Pro
            35                  40                  45

Tyr Val Glu Gln Lys Ser Ile Pro Glu Arg Ile Glu Met Ala Ala Glu
        50                  55                  60

Met Ala Lys Phe Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Ala
                85                  90                  95

Gly Ile Arg Leu Val Ala Val Cys Leu Ser Leu Phe Tyr Asp Lys Ile
            100                 105                 110

Phe Glu Phe Gly Ser Leu Ser Asn Pro Tyr Glu Lys Tyr Arg Lys Val
            115                 120                 125

Ala Tyr Glu Arg Leu Val Asn Gly Leu Lys Leu Val Lys Glu Ala Asn
            130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
            195                 200                 205

Gly Ile Leu Ala Ala Arg Asp Ile Glu Ala Arg Leu Lys Asn Pro Glu
            210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
            275                 280                 285

Trp Asp Ser Thr Glu Ala Leu Leu Tyr Thr Leu Lys Met Val Gly Tyr
290                 295                 300

Gln Gly Tyr Phe Gly Ile Asp Ile Asn Pro Glu Arg Met Pro Val Ile
            305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Gly Asn His Lys
            355                 360                 365

<210> SEQ ID NO 7
<211> LENGTH: 368
<212> TYPE: PRT
<213> ORGANISM: Dictyoglomus thermophilum

<400> SEQUENCE: 7

Met Pro Phe Val Asp His Arg Asn Gln Lys Ile Arg Arg Ser Lys Glu
1               5                   10                  15

Glu Leu Leu Lys His Met Gln Thr Phe Lys Leu Asp Leu Lys Phe Ser
            20                  25                  30
```

Val Gly Ile Trp Tyr Phe Thr Pro Gly Gly Arg Phe His Glu Pro
            35                  40                  45

Tyr Val Glu Gln Lys Gly Ile Pro Glu Arg Ile Glu Met Ala Ala Glu
    50                  55                  60

Met Ala Lys Tyr Gly Val Lys Gly Ile Glu Ala His Tyr Pro Ala Glu
65                  70                  75                  80

Val Asn Glu Glu Asn Leu His Leu Tyr Lys Gln Leu Glu Lys Glu Thr
                85                  90                  95

Gly Ile Arg Leu Val Ala Val Gly Leu Ser Leu Phe Tyr Asp Lys Ile
            100                 105                 110

Phe Glu Phe Gly Ser Leu Ser Asn Pro Tyr Glu Lys Tyr Arg Lys Ile
            115                 120                 125

Ala Tyr Glu Arg Leu Val Asn Gly Leu Lys Leu Val Lys Glu Ala Asn
            130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
            195                 200                 205

Gly Ile Leu Ala Ala Arg Asp Ile Glu Ala Arg Leu Lys Asn Pro Glu
            210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
            275                 280                 285

Trp Asp Ser Thr Glu Ala Leu Leu Tyr Thr Leu Lys Met Val Gly Tyr
290                 295                 300

Gln Gly Tyr Phe Gly Ile Asp Ile Asn Pro Glu Arg Ile Pro Val Val
305                 310                 315                 320

Lys Ala Ile Glu Ile Asn Thr Lys Val Leu Gln Ile Met Asn Glu Arg
            325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Arg
            355                 360                 365

<210> SEQ ID NO 8
<211> LENGTH: 368
<212> TYPE: PRT
<213> ORGANISM: Dictyoglomus thermophilum

<400> SEQUENCE: 8

Met Pro Phe Val Asp His Arg Asn Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
            35                  40                  45

Tyr Val Glu Gln Lys Gly Ile Pro Glu Arg Ile Glu Met Ala Ala Glu
            50                  55                  60

Met Ala Lys Tyr Gly Val Lys Gly Ile Glu Ala His Tyr Pro Ala Glu
 65                  70                  75                  80

Val Asn Glu Glu Asn Leu His Leu Tyr Lys Gln Leu Glu Lys Glu Thr
                 85                  90                  95

Gly Ile Arg Leu Val Ala Val Ser Leu Ser Leu Phe Tyr Asp Lys Ile
                100                 105                 110

Phe Glu Phe Gly Ser Leu Ser Asn Pro Tyr Glu Lys Tyr Arg Lys Ile
            115                 120                 125

Ala Tyr Glu Arg Leu Val Asn Gly Leu Lys Leu Val Lys Glu Ala Asn
            130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
            195                 200                 205

Gly Ile Leu Ala Ala Arg Asp Ile Glu Ala Arg Leu Lys Asn Pro Glu
210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
            275                 280                 285

Trp Asp Ser Thr Glu Ala Leu Leu Tyr Thr Leu Lys Met Val Gly Tyr
290                 295                 300

Gln Gly Tyr Phe Gly Ile Asp Ile Asn Pro Glu Arg Ile Pro Val Val
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Arg
            355                 360                 365

<210> SEQ ID NO 9
<211> LENGTH: 368
<212> TYPE: PRT
<213> ORGANISM: Dictyoglomus thermophilum

<400> SEQUENCE: 9

Met Pro Phe Val Asp His Arg Asn Gln Lys Ile Arg Arg Ser Lys Glu
1               5                   10                  15

Glu Leu Leu Lys His Met Gln Thr Phe Lys Leu Asp Leu Lys Phe Ser
            20                  25                  30

Val Gly Ile Trp Tyr Phe Thr Pro Gly Gly Arg Phe His Glu Pro
            35                  40                  45

Tyr Val Glu Gln Lys Gly Ile Pro Glu Arg Ile Glu Met Ala Ala Glu

```
            50                  55                  60
Met Ala Lys Tyr Gly Val Lys Gly Ile Glu Ala His Tyr Pro Ala Glu
 65                  70                  75                  80

Val Asn Glu Glu Asn Leu His Leu Tyr Lys Gln Leu Glu Lys Glu Thr
                 85                  90                  95

Gly Ile Arg Leu Val Ala Val Ala Leu Ser Leu Phe Tyr Asp Lys Ile
            100                 105                 110

Phe Glu Phe Gly Ser Leu Ser Asn Pro Tyr Glu Lys Tyr Arg Lys Ile
            115                 120                 125

Ala Tyr Glu Arg Leu Val Asn Gly Leu Lys Leu Val Lys Glu Ala Asn
            130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
            165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
            195                 200                 205

Gly Ile Leu Ala Ala Arg Asp Ile Glu Ala Arg Leu Lys Asn Pro Glu
            210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
            245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
            275                 280                 285

Trp Asp Ser Thr Glu Ala Leu Leu Tyr Thr Leu Lys Met Val Gly Tyr
290                 295                 300

Gln Gly Tyr Phe Gly Ile Asp Ile Asn Pro Glu Arg Ile Pro Val Val
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Arg
            355                 360                 365

<210> SEQ ID NO 10
<211> LENGTH: 368
<212> TYPE: PRT
<213> ORGANISM: Dictyoglomus thermophilum

<400> SEQUENCE: 10

Met Pro Phe Val Asp His Arg Asn Gln Lys Ile Arg Arg Ser Lys Glu
 1               5                  10                  15

Glu Leu Leu Lys His Met Gln Thr Phe Lys Leu Asp Leu Lys Phe Ser
                20                  25                  30

Val Gly Ile Trp Tyr Phe Thr Pro Gly Gly Arg Phe His Glu Pro
            35                  40                  45

Tyr Val Glu Gln Lys Gly Ile Pro Glu Arg Ile Glu Met Ala Ala Glu
 50                  55                  60
```

```
Met Ala Lys Tyr Gly Val Lys Gly Ile Glu Ala His Tyr Pro Ala Glu
 65                  70                  75                  80

Val Asn Glu Glu Asn Leu His Leu Tyr Lys Gln Leu Glu Lys Glu Thr
                 85                  90                  95

Gly Ile Arg Leu Val Ala Val Cys Leu Ser Leu Phe Tyr Asp Lys Ile
            100                 105                 110

Phe Glu Phe Gly Ser Leu Ser Asn Pro Tyr Glu Lys Tyr Arg Lys Ile
        115                 120                 125

Ala Tyr Glu Arg Leu Val Asn Gly Leu Lys Leu Val Lys Glu Ala Asn
    130                 135                 140

Ala Asp Ile Cys Ile Ile Trp Pro Gly Ile Asp Gly Tyr Thr Tyr Ser
145                 150                 155                 160

Tyr Gly His Leu Tyr Tyr His Met Trp Asp Thr Phe Glu Glu Leu Val
                165                 170                 175

Ala Gln Ala Met Asp Glu Val Pro Gly Val Gln Val Ala Ile Glu Pro
            180                 185                 190

Lys Pro Tyr Glu Pro Ala Pro Asn Asn Ile Tyr Arg Thr Thr Ala Asp
        195                 200                 205

Gly Ile Leu Ala Ala Arg Asp Ile Glu Ala Arg Leu Lys Asn Pro Glu
    210                 215                 220

Asn Leu Lys Leu Leu Gln Glu Gly His Ala Leu Val Gly Leu Asn Pro
225                 230                 235                 240

Glu Val Gly His Val Arg Met Gly Phe Glu Asp Leu Pro Tyr Ala Tyr
                245                 250                 255

Ala Arg Val Ala Arg Glu Gly Arg Leu Phe His Thr His Trp Asn Ser
            260                 265                 270

Gln Pro Leu Gly Asn Tyr Asp Gln Asp Leu Asn Ile Gly Val Val Asp
        275                 280                 285

Trp Asp Ser Thr Glu Ala Leu Leu Tyr Thr Leu Lys Met Val Gly Tyr
    290                 295                 300

Gln Gly Tyr Phe Gly Ile Asp Ile Asn Pro Glu Arg Ile Pro Val Val
305                 310                 315                 320

Lys Ala Ile Glu Ile Asn Thr Lys Val Leu Gln Ile Met Asn Glu Arg
                325                 330                 335

Ile Glu Arg Leu Pro His Asp Arg Ile Ile Glu Cys Tyr Phe Asp Pro
            340                 345                 350

Glu Asn His Arg Gly Glu Leu Glu Leu Ile Leu Ala Glu Asn His Arg
        355                 360                 365

<210> SEQ ID NO 11
<211> LENGTH: 1104
<212> TYPE: DNA
<213> ORGANISM: Dictyoglomus thermophilum

<400> SEQUENCE: 11
atgccgtttg ttgatcatcg tgcacagaaa attcgtcgca gcaaagaaga actgctgaaa      60
catatgcaga ccttcaaact ggatctgaaa tttagcgtgg catctggta ttttacaccg      120 ggtggtggtc gttttcatga accgtatgtt gaacagaaaa gcattccgga acgtattgaa      180
atggcagcag aaatggcaaa atttggcgtg aaaggtattg aagcacatta tccggctgaa      240
gtgaatgaag aaaatctgca cctgtataaa cagctggaaa agaagcagg tattcgtctg      300 gttgcagttc gcctgagcct gttttatgat aaaatctttg aatttggcag cctgagcaac      360
ccgtatgaaa aatatcgtaa agttgcctat gaacgcctgg tgaatggtct gaaactggtt      420
```

| | |
|---|---|
| aaagaagcaa acgccgatat ttgcattatt tggcctggta ttgatggcta tacctatagc | 480 |
| tatggtcacc tgtattatca catgtgggat acctttgaag aactggttgc acaggcaatg | 540 |
| gatgaagttc cgggtgttca ggttgcaatt gaaccgaaac cgtatgaacc ggcaccgaat | 600 |
| aacatttatc gtaccaccgc agatggtatt ctggcagcac gtgatattga agcgcgtctg | 660 |
| aaaaatccgg aaaacctgaa actgctgcaa gaaggtcacg cactggttgg tctgaatccg | 720 |
| gaagttggtc atgttcgtat gggttttgaa gatctgccgt atgcatatgc ccgtgttgca | 780 |
| cgtgaaggtc gtctgtttca tacccattgg aatagccagc cgctgggtaa ttatgatcag | 840 |
| gatctgaata ttggtgtggt ggattgggat agcaccgaag cactgctgta tacccctgaaa | 900 |
| atggttggtt atcagggcta ttttggcatc gatatcaatc cggaacgcat gccggttatt | 960 |
| aaagccattg aaattaacac caaagtgctg cagattatga cgaacgcat tgaacgtctg | 1020 |
| ccgcatgatc gtattattga gtgttatttt gaccctgaga atcatcgtgg tgaactggaa | 1080 |
| ctgattctgg ccgaaaatca taaa | 1104 |

<210> SEQ ID NO 12
<211> LENGTH: 1104
<212> TYPE: DNA
<213> ORGANISM: Dictyoglomus thermophilum

<400> SEQUENCE: 12

| | |
|---|---|
| atgccgtttg tggatcatcg taatcagaaa attcgtcgca gcaaagaaga actgctgaaa | 60 |
| cacatgcaga cctttaaact ggatctgaaa tttagcgttg gcatctggta ttttaccccct | 120 |
| ggtggtggtc gttttcatga accgtatgtt gaacagaaag gtattccgga acgtattgaa | 180 |
| atggcagcag aaatggcaaa atatggcgtt aaaggtatcg aagcacatta tccggctgaa | 240 |
| gtgaatgaag aaaatctgca cctgtataaa cagctggaaa agaaaccgg tattcgtctg | 300 |
| gttgcagttc cgctgagcct gttttatgat aaaatctttg aatttggcag cctgagcaac | 360 |
| ccgtatgaaa aatatcgtaa aattgcctat gaatgcctgg tgaatggtct gaaactggtt | 420 |
| aaagaagcaa acgccgatat ttgcattatt tggcctggta ttgatggcta tacctatagc | 480 |
| tatggtcacc tgtattatca catgtgggat acctttgaag aactggttgc acaggcaatg | 540 |
| gatgaagttc cgggtgttca ggttgcaatt gaaccgaaac cgtatgaacc ggcaccgaat | 600 |
| aacatttatc gtaccaccgc agatggtatt ctggcagcac gtgatattga agcacgtctg | 660 |
| aaaaatccgg aaaacctgaa actgctgcaa gaaggtcacg cactggttgg tctgaatccg | 720 |
| gaagttggtc atgttcgtat gggttttgaa gatctgccgt atgcctatgc acgtgttgca | 780 |
| cgtgaaggtc gtctgtttca tacccattgg aatagccagc cgctgggtaa ttatgatcag | 840 |
| gatctgaata ttggtgtggt ggattgggat agcaccgaag cactgctgta tacccctgaaa | 900 |
| atggttggtt atcagggcta ttttggcatc gatattaatc cggaacgcat tccggttgtt | 960 |
| aaagccattg aaattaacac caaagtgctg cagattatga cgaacgcat tgaacgtctg | 1020 |
| ccgcatgatc gtattattga gtgttatttt gaccccgaaa atcatcgtgg tgaactggaa | 1080 |
| ctgattctgg cggaaaacca tcgt | 1104 |

<210> SEQ ID NO 13
<211> LENGTH: 1104
<212> TYPE: DNA
<213> ORGANISM: Dictyoglomus thermophilum

<400> SEQUENCE: 13

| | |
|---|---|
| atgccgtttg ttgatcatcg tgcacagaaa attcgtcgca gcaaagaaga actgctgaaa | 60 |

```
catatgcaga ccttcaaact ggatctgaaa tttagcgtgg gcatctggta ttttacaccg    120
ggtggtggtc gttttcatga accgtatgtt gaacagaaaa gcattccgga acgtattgaa    180
atggcagcag aaatggcaaa atttggcgtg aaaggtattg aagcacatta tccggctgaa    240
gtgaatgaag aaaatctgca cctgtataaa cagctggaaa agaagcagg tattcgtctg     300 gttgcagttg gtctgagcct gttttatgat aaaatctttg aatttggcag cctgagcaac    360
ccgtatgaaa aatatcgtaa agttgcctat gaacgcctgg tgaatggtct gaaactggtt    420
aaagaagcaa acgccgatat ttgcattatt tggcctggta ttgatggcta tacctatagc    480
tatggtcacc tgtattatca catgtgggat accttgaag aactggttgc acaggcaatg     540
gatgaagttc cgggtgttca ggttgcaatt gaaccgaaac cgtatgaacc ggcaccgaat    600
aacatttatc gtaccaccgc agatggtatt ctggcagcac gtgatattga agcgcgtctg    660
aaaaatccgg aaaacctgaa actgctgcaa gaaggtcacg cactggttgg tctgaatccg    720
gaagttggtc atgttcgtat gggttttgaa gatctgccgt atgcatatgc ccgtgttgca    780
cgtgaaggtc gtctgtttca tacccattgg aatagccagc cgctgggtaa ttatgatcag    840
gatctgaata ttggtgtggt ggattgggat agcaccgaag cactgctgta taccctgaaa    900
atggttggtt atcagggcta ttttggcatc gatatcaatc cggaacgcat gccggttatt    960
aaagccattg aaattaacac caaagtgctg cagattatga cgaacgcat tgaacgtctg    1020 ccgcatgatc gtattattga gtgttatttt gaccctgaga tcatcgtgg tgaactggaa   1080 ctgattctgg ccgaaaatca taaa                                            1104
```

```
<210> SEQ ID NO 14
<211> LENGTH: 1104
<212> TYPE: DNA
<213> ORGANISM: Dictyoglomus thermophilum

<400> SEQUENCE: 14
atgccgtttg ttgatcatcg tgcacagaaa attcgtcgca gcaaagaaga actgctgaaa    60
catatgcaga ccttcaaact ggatctgaaa tttagcgtgg gcatctggta ttttacaccg    120
ggtggtggtc gttttcatga accgtatgtt gaacagaaaa gcattccgga acgtattgaa    180
atggcagcag aaatggcaaa atttggcgtg aaaggtattg aagcacatta tccggctgaa    240
gtgaatgaag aaaatctgca cctgtataaa cagctggaaa agaagcagg tattcgtctg     300 gttgcagttt ctctgagcct gttttatgat aaaatctttg aatttggcag cctgagcaac    360
ccgtatgaaa aatatcgtaa agttgcctat gaacgcctgg tgaatggtct gaaactggtt    420
aaagaagcaa acgccgatat ttgcattatt tggcctggta ttgatggcta tacctatagc    480
tatggtcacc tgtattatca catgtgggat accttgaag aactggttgc acaggcaatg     540
gatgaagttc cgggtgttca ggttgcaatt gaaccgaaac cgtatgaacc ggcaccgaat    600
aacatttatc gtaccaccgc agatggtatt ctggcagcac gtgatattga agcgcgtctg    660
aaaaatccgg aaaacctgaa actgctgcaa gaaggtcacg cactggttgg tctgaatccg    720
gaagttggtc atgttcgtat gggttttgaa gatctgccgt atgcatatgc ccgtgttgca    780
cgtgaaggtc gtctgtttca tacccattgg aatagccagc cgctgggtaa ttatgatcag    840
gatctgaata ttggtgtggt ggattgggat agcaccgaag cactgctgta taccctgaaa    900
atggttggtt atcagggcta ttttggcatc gatatcaatc cggaacgcat gccggttatt    960
aaagccattg aaattaacac caaagtgctg cagattatga cgaacgcat tgaacgtctg    1020
```

```
ccgcatgatc gtattattga gtgttatttt gaccctgaga atcatcgtgg tgaactggaa    1080
ctgattctgg ccgaaaatca taaa                                          1104
```

<210> SEQ ID NO 15
<211> LENGTH: 1104
<212> TYPE: DNA
<213> ORGANISM: Dictyoglomus thermophilum

<400> SEQUENCE: 15

```
atgccgtttg ttgatcatcg tgcacagaaa attcgtcgca gcaaagaaga actgctgaaa     60
catatgcaga ccttcaaact ggatctgaaa tttagcgtgg gcatctggta ttttacaccg    120
ggtggtggtc gttttcatga accgtatgtt gaacagaaaa gcattccgga cgtattgaa    180 atggcagcag aaatggcaaa atttggcgtg aaaggtattg aagcacatta tccggctgaa    240
gtgaatgaag aaaatctgca cctgtataaa cagctggaaa agaagcagg tattcgtctg    300 gttgcagttg ctctgagcct gttttatgat aaaatctttg aatttggcag cctgagcaac    360
ccgtatgaaa aatatcgtaa agttgcctat gaacgcctgg tgaatggtct gaaactggtt    420
aaagaagcaa acgccgatat ttgcattatt tggcctggta ttgatggcta tacctatagc    480
tatggtcacc tgtattatca catgtgggat acctttgaag aactggttgc acaggcaatg    540
gatgaagttc cgggtgttca ggttgcaatt gaaccgaaac cgtatgaacc ggcaccgaat    600
aacatttatc gtaccaccgc agatggtatt ctggcagcac gtgatattga agcgcgtctg    660
aaaaatccgg aaaacctgaa actgctgcaa gaaggtcacg cactggttgg tctgaatccg    720
gaagttggtc atgttcgtat gggttttgaa gatctgccgt atgcatatgc ccgtgttgca    780
cgtgaaggtc gtctgtttca tacccattgg aatagccagc cgctgggtaa ttatgatcag    840
gatctgaata ttggtgtggt ggattgggat agcaccgaag cactgctgta tacctgaaa    900 atggttggtt atcagggcta ttttggcatc gatatcaatc ggaacgcat gccggttatt    960 aaagccattg aaattaacac caaagtgctg cagattatga cgaacgcat gaacgtctg   1020 ccgcatgatc gtattattga gtgttatttt gaccctgaga atcatcgtgg tgaactggaa   1080
ctgattctgg ccgaaaatca taaa                                          1104
```

<210> SEQ ID NO 16
<211> LENGTH: 1104
<212> TYPE: DNA
<213> ORGANISM: Dictyoglomus thermophilum

<400> SEQUENCE: 16

```
atgccgtttg ttgatcatcg tgcacagaaa attcgtcgca gcaaagaaga actgctgaaa     60
catatgcaga ccttcaaact ggatctgaaa tttagcgtgg gcatctggta ttttacaccg    120
ggtggtggtc gttttcatga accgtatgtt gaacagaaaa gcattccgga cgtattgaa    180 atggcagcag aaatggcaaa atttggcgtg aaaggtattg aagcacatta tccggctgaa    240
gtgaatgaag aaaatctgca cctgtataaa cagctggaaa agaagcagg tattcgtctg    300 gttgcagttt gcctgagcct gttttatgat aaaatctttg aatttggcag cctgagcaac    360
ccgtatgaaa aatatcgtaa agttgcctat gaacgcctgg tgaatggtct gaaactggtt    420
aaagaagcaa acgccgatat ttgcattatt tggcctggta ttgatggcta tacctatagc    480
tatggtcacc tgtattatca catgtgggat acctttgaag aactggttgc acaggcaatg    540
gatgaagttc cgggtgttca ggttgcaatt gaaccgaaac cgtatgaacc ggcaccgaat    600
aacatttatc gtaccaccgc agatggtatt ctggcagcac gtgatattga agcgcgtctg    660
```

```
aaaaatccgg aaaacctgaa actgctgcaa gaaggtcacg cactggttgg tctgaatccg    720
gaagttggtc atgttcgtat gggttttgaa gatctgccgt atgcatatgc ccgtgttgca    780
cgtgaaggtc gtctgtttca tacccattgg aatagccagc cgctgggtaa ttatgatcag    840
gatctgaata ttggtgtggt ggattgggat agcaccgaag cactgctgta tacccctgaaa   900 atggttggtt atcagggcta ttttggcatc gatatcaatc cggaacgcat gccggttatt    960
aaagccattg aaattaacac caaagtgctg cagattatga cgaacgcat tgaacgtctg   1020 ccgcatgatc gtattattga gtgttatttt gaccctgaga atcatcgtgg tgaactggaa   1080
ctgattctgg ccgaaaatca taaa                                           1104

<210> SEQ ID NO 17
<211> LENGTH: 1104
<212> TYPE: DNA
<213> ORGANISM: Dictyoglomus thermophilum

<400> SEQUENCE: 17
atgccgtttg tggatcatcg taatcagaaa attcgtcgca gcaaagaaga actgctgaaa     60
cacatgcaga cctttaaact ggatctgaaa tttagcgttg gcatctggta ttttacccct    120
ggtggtggtc gttttcatga accgtatgtt gaacagaaag gtattccgga acgtattgaa    180
atggcagcag aaatggcaaa atatggcgtt aaaggtatcg aagcacatta tccggctgaa    240
gtgaatgaag aaaatctgca cctgtataaa cagctggaaa agaaaccgg tattcgtctg    300 gttgcagttg gtctgagcct gttttatgat aaaatctttg aatttggcag cctgagcaac    360
ccgtatgaaa aatatcgtaa aattgcctat gaacgcctgg tgaatggtct gaaactggtt    420
aaagaagcaa cgccgatat ttgcattatt tggcctggta ttgatggcta tacctatagc    480
tatggtcacc tgtattatca catgtgggat acctttgaag aactggttgc acaggcaatg    540
gatgaagttc cgggtgttca ggttgcaatt gaaccgaaac cgtatgaacc ggcaccgaat    600
aacatttatc gtaccaccgc agatggtatt ctggcagcac gtgatattga agcacgtctg    660
aaaaatccgg aaaacctgaa actgctgcaa gaaggtcacg cactggttgg tctgaatccg    720
gaagttggtc atgttcgtat gggttttgaa gatctgccgt atgcctatgc acgtgttgca    780
cgtgaaggtc gtctgtttca tacccattgg aatagccagc cgctgggtaa ttatgatcag    840
gatctgaata ttggtgtggt ggattgggat agcaccgaag cactgctgta tacccctgaaa   900 atggttggtt atcagggcta ttttggcatc gatattaatc cggaacgcat tccggttgtt    960
aaagccattg aaattaacac caaagtgctg cagattatga cgaacgcat tgaacgtctg   1020 ccgcatgatc gtattattga gtgttatttt gaccccgaaa atcatcgtgg tgaactggaa   1080
ctgattctgg cggaaaacca tcgt                                           1104

<210> SEQ ID NO 18
<211> LENGTH: 1104
<212> TYPE: DNA
<213> ORGANISM: Dictyoglomus thermophilum

<400> SEQUENCE: 18
atgccgtttg tggatcatcg taatcagaaa attcgtcgca gcaaagaaga actgctgaaa     60
cacatgcaga cctttaaact ggatctgaaa tttagcgttg gcatctggta ttttacccct    120
ggtggtggtc gttttcatga accgtatgtt gaacagaaag gtattccgga acgtattgaa    180
atggcagcag aaatggcaaa atatggcgtt aaaggtatcg aagcacatta tccggctgaa    240
```

-continued

```
gtgaatgaag aaaatctgca cctgtataaa cagctggaaa agaaaccgg tattcgtctg      300 gttgcagttt ctctgagcct gttttatgat aaaatctttg aatttggcag cctgagcaac    360
ccgtatgaaa aatatcgtaa aattgcctat gaacgcctgg tgaatggtct gaaactggtt    420
aaagaagcaa acgccgatat ttgcattatt tggcctggta ttgatggcta tacctatagc    480
tatggtcacc tgtattatca catgtgggat acctttgaag aactggttgc acaggcaatg    540
gatgaagttc cgggtgttca ggttgcaatt gaaccgaaac cgtatgaacc ggcaccgaat    600
aacatttatc gtaccaccgc agatggtatt ctggcagcac gtgatattga agcacgtctg    660
aaaaatccgg aaaacctgaa actgctgcaa aaggtcacg cactggttgg tctgaatccg     720
gaagttggtc atgttcgtat gggttttgaa gatctgccgt atgcctatgc acgtgttgca    780
cgtgaaggtc gtctgtttca tacccattgg aatagccagc cgctgggtaa ttatgatcag    840
gatctgaata ttggtgtggt ggattgggat agcaccgaag cactgctgta taccctgaaa    900
atggttggtt atcagggcta ttttggcatc gatattaatc ggaacgcat tccggttgtt     960 aaagccattg aaattaacac caaagtgctg cagattatga cgaacgcat tgaacgtctg     1020 ccgcatgatc gtattattga gtgttatttt gaccccgaaa atcatcgtgg tgaactggaa    1080
ctgattctgg cggaaaacca tcgt                                           1104
```

<210> SEQ ID NO 19
<211> LENGTH: 1104
<212> TYPE: DNA
<213> ORGANISM: Dictyoglomus thermophilum

<400> SEQUENCE: 19

```
atgccgtttg tggatcatcg taatcagaaa attcgtcgca gcaaagaaga actgctgaaa     60
cacatgcaga cctttaaact ggatctgaaa tttagcgttg gcatctggta ttttaccccct   120 ggtggtggtc gttttcatga accgtatgtt gaacagaaag gtattccgga acgtattgaa    180
atggcagcag aaatggcaaa atatggcgtt aaaggtatcg aagcacatta tccggctgaa    240
gtgaatgaag aaaatctgca cctgtataaa cagctggaaa agaaaccgg tattcgtctg     300 gttgcagttt ctctgagcct gttttatgat aaaatctttg aatttggcag cctgagcaac    360
ccgtatgaaa aatatcgtaa aattgcctat gaacgcctgg tgaatggtct gaaactggtt    420
aaagaagcaa acgccgatat ttgcattatt tggcctggta ttgatggcta tacctatagc    480
tatggtcacc tgtattatca catgtgggat acctttgaag aactggttgc acaggcaatg    540
gatgaagttc cgggtgttca ggttgcaatt gaaccgaaac cgtatgaacc ggcaccgaat    600
aacatttatc gtaccaccgc agatggtatt ctggcagcac gtgatattga agcacgtctg    660
aaaaatccgg aaaacctgaa actgctgcaa aaggtcacg cactggttgg tctgaatccg     720
gaagttggtc atgttcgtat gggttttgaa gatctgccgt atgcctatgc acgtgttgca    780
cgtgaaggtc gtctgtttca tacccattgg aatagccagc cgctgggtaa ttatgatcag    840
gatctgaata ttggtgtggt ggattgggat agcaccgaag cactgctgta taccctgaaa    900
atggttggtt atcagggcta ttttggcatc gatattaatc ggaacgcat tccggttgtt     960 aaagccattg aaattaacac caaagtgctg cagattatga cgaacgcat tgaacgtctg     1020 ccgcatgatc gtattattga gtgttatttt gaccccgaaa atcatcgtgg tgaactggaa    1080
ctgattctgg cggaaaacca tcgt                                           1104
```

<210> SEQ ID NO 20
<211> LENGTH: 1104

<212> TYPE: DNA
<213> ORGANISM: Dictyoglomus thermophilum

<400> SEQUENCE: 20

```
atgccgtttg tggatcatcg taatcagaaa attcgtcgca gcaaagaaga actgctgaaa      60
cacatgcaga cctttaaact ggatctgaaa tttagcgttg gcatctggta ttttacccct     120
ggtggtggtc gttttcatga accgtatgtt gaacagaaag gtattccgga acgtattgaa     180
atggcagcag aaatggcaaa atatggcgtt aaaggtatcg aagcacatta tccggctgaa     240
gtgaatgaag aaaatctgca cctgtataaa cagctggaaa agaaaccgg tattcgtctg      300
gttgcagttt gcctgagcct gttttatgat aaaatctttg aatttggcag cctgagcaac     360
ccgtatgaaa aatatcgtaa aattgcctat gaacgcctgg tgaatggtct gaaactggtt     420
aaagaagcaa acgccgatat ttgcattatt tggcctggta ttgatggcta tacctatagc     480
tatggtcacc tgtattatca catgtgggat acctttgaag aactggttgc acaggcaatg     540
gatgaagttc cgggtgttca ggttgcaatt gaaccgaaac cgtatgaacc ggcaccgaat     600
aacatttatc gtaccaccgc agatggtatt ctggcagcac gtgatattga agcacgtctg     660
aaaaatccgg aaaacctgaa actgctgcaa gaaggtcacg cactggttgg tctgaatccg     720
gaagttggtc atgttcgtat gggttttgaa gatctgccgt atgcctatgc acgtgttgca     780
cgtgaaggtc gtctgtttca tacccattgg aatagccagc cgctgggtaa ttatgatcag     840
gatctgaata ttggtgtggt ggattgggat agcaccgaag cactgctgta taccctgaaa     900
atggttggtt atcagggcta ttttggcatc gatattaatc cggaacgcat tccggttgtt     960
aaagccattg aaattaacac caaagtgctg cagattatga cgaacgcat tgaacgtctg    1020
ccgcatgatc gtattattga gtgttatttt gaccccgaaa atcatcgtgg tgaactggaa    1080
ctgattctgg cggaaaacca tcgt                                           1104
```